(12) United States Patent
Burman et al.

(10) Patent No.: US 12,678,047 B2
(45) Date of Patent: Jul. 14, 2026

(54) SYSTEM AND METHOD FOR DETERMINING INFRASPECTRAL MARKERS USING TRANSDERMAL INFRARED OPTICS

(71) Applicant: RCE Technologies, Inc., Carlsbad, CA (US)

(72) Inventors: Atandra Burman, Bermuda Dunes, CA (US); Jitto Titus, Acworth, GA (US); Siddharth Biswal, Atlanta, GA (US)

(73) Assignee: RCE Technologies, Ine, Carlsbad, CA (US)

( * ) Notice: Subject to any disclaimer, the term of this patent is extended or adjusted under 35 U.S.C. 154(b) by 0 days.

(21) Appl. No.: 18/656,821

(22) Filed: May 7, 2024

(65) Prior Publication Data

US 2024/0293027 A1      Sep. 5, 2024

Related U.S. Application Data

(63) Continuation of application No. PCT/US2022/049103, filed on Nov. 7, 2022, which is a continuation-in-part of application No. 17/537,932, filed on Nov. 30, 2021, now Pat. No. 12,201,419.

(60) Provisional application No. 63/346,552, filed on May 27, 2022, provisional application No. 63/276,594, filed on Nov. 7, 2021.

(51) Int. Cl.
*A61B 5/00* (2006.01)

(52) U.S. Cl.
CPC .......... *A61B 5/0062* (2013.01); *A61B 5/0075* (2013.01); *A61B 5/4839* (2013.01); *A61B*

5/4842 (2013.01); *A61B 5/7275* (2013.01); *A61B 2562/0238* (2013.01)

(58) Field of Classification Search
CPC ... A61B 5/0062; A61B 5/0075; A61B 5/4839; A61B 5/4842; A61B 5/7275; A61B 2562/0238; A61B 5/742; A61B 5/1455; A61B 5/6824; A61B 5/6831; A61B 5/14546
See application file for complete search history.

(56) References Cited

U.S. PATENT DOCUMENTS

| | | | |
|---|---|---|---|
| 5,978,691 | A | 11/1999 | Mills |
| 11,969,577 | B1 | 4/2024 | Sahani et al. |
| 2012/0253149 | A1 | 10/2012 | Steuer |

(Continued)

OTHER PUBLICATIONS

International Search report for International Application No. PCT/US2022/49103, dated Feb. 28, 2023.

*Primary Examiner* — Serkan Akar
(74) *Attorney, Agent, or Firm* — Quinn IP Law

(57) ABSTRACT

One or more aspects of the technical solutions described herein facilitate using transdermal infrared optics to discover infraspectral markers. The infraspectral markers can predict presence/absence of one or more physiological state in a subject. One or more aspects of the technical solutions described herein further facilitate continuous monitoring and prediction of trends of a physiological state of a subject using non-invasive transdermal infrared optics. Further, one or more aspects of the technical solutions described herein facilitate personalized triage of and alerts for a subject based on continuous monitoring of non-invasive transdermal optical infraspectral markers.

18 Claims, 7 Drawing Sheets

(56) References Cited

U.S. PATENT DOCUMENTS

| | | | |
|---|---|---|---|
| 2015/0112168 A1* | 4/2015 | Conrad | G01R 33/24 |
| | | | 600/309 |
| 2015/0268251 A1 | 9/2015 | Zaugg et al. | |
| 2016/0305877 A1 | 10/2016 | Titus et al. | |
| 2017/0112991 A1 | 4/2017 | Pudil et al. | |
| 2017/0173262 A1 | 6/2017 | Veltz | |
| 2018/0364163 A1* | 12/2018 | Titus | G01N 21/3581 |
| 2020/0069860 A1 | 3/2020 | Rammo et al. | |
| 2020/0118679 A1* | 4/2020 | Burman | A61B 5/0075 |
| 2020/0206422 A1 | 7/2020 | Cassim | |
| 2020/0241019 A1 | 7/2020 | Kim | |
| 2021/0195891 A1 | 7/2021 | Uygun et al. | |
| 2021/0391081 A1 | 12/2021 | Goldner et al. | |
| 2022/0136956 A1 | 5/2022 | Roberts et al. | |
| 2023/0272056 A1 | 8/2023 | Hsieh et al. | |
| 2023/0386656 A1 | 11/2023 | Huneker et al. | |

* cited by examiner

SYSTEM AND METHOD FOR DETERMINING INFRASPECTRAL MARKERS USING TRANSDERMAL INFRARED OPTICS

CROSS REFERENCE TO RELATED APPLICATIONS

This Application claims the benefit of International Application Ser. No. PCT/US2022/049103 which claims the benefit of U.S. Non-Provisional application Ser. No. 17/537,932 filed Nov. 30, 2021, U.S. Provisional Application No. 63/276,594 filed Nov. 7, 2021, and U.S. Provisional Application No. 63/346,552 filed May 27, 2022, the contents of which are incorporated by reference herein in their entireties.

TECHNICAL FIELD

The present disclosure generally relates to technical solutions using spectroscopy for the discovery and detection of biomarkers in a non-invasive, transdermal manner.

BACKGROUND

Over ten million symptomatic patients present with chest pain in emergency departments in the United States each year. Over 80% of these are due to non-cardiac causes, resulting in an unnecessary burden in the emergency departments. This reveals a need for non-invasive detection techniques that can streamline the emergency department workflows, preferably with a rapid testing mechanism for timely analysis. Furthermore, one out of five myocardial infarctions is asymptomatic (silent), leading to nearly 200,000 silent myocardial infarctions each year in the US. Therefore, the development of new technologies that can allow early non-invasive detection of myocardial injury is imperative.

State-of-the-art for troponin assays involve the use of two or more antibodies, one of which is labeled, typically with a chemiluminescent tag, which add another level of complexity in the analysis. While recent point-of-care (POC) solutions have reduced the time required to obtain test results, there still remains a dependency upon blood draws coupled with lower analytical sensitivity compared to central laboratory testing. This has resulted in limited application of such solutions toward effective discharge from emergency departments. Accordingly, improved solutions are desired to improve emergency room discharge and patient diagnostics and evaluation.

SUMMARY

One or more aspects of the technical solutions described herein facilitate using transdermal infrared optics to discover infraspectral markers. The infraspectral markers, also referred to herein as inframarkers, can predict presence/absence of one or more physiological states in a subject. One or more aspects of the technical solutions described herein further facilitate continuous monitoring and prediction of trends of a physiological state of a subject using non-invasive transdermal infrared optics to generate infrasensor data, which is analyzed for inframarkers. Further, one or more aspects of the technical solutions described herein facilitate personalized triage of and alerts for a subject based on continuous non-invasive transdermal monitoring of optical infraspectral markers of the subject.

According to one or more aspects of the technical solution described herein, a system includes a transdermal optical monitoring device, and an analysis system in communication with the transdermal optical monitoring device. The analysis system performs a method that includes receiving, from the transdermal optical monitoring device, a predetermined number of optical scans, each optical scan comprising data indicative of absorption of light by a subject, the absorption caused in response to the transdermal optical monitoring device transmitting light pulses towards the subject in a transdermal manner. The method further includes establishing a baseline measurement for an inframarker based on the data from the predetermined number of optical scans, the inframarker is indicative of a biomarker of a physiological state of the subject, the inframarker is based on one or more measurements from an optical scan. The method further includes receiving, from the optical monitoring device, a first optical scan comprising a first measurement of the inframarker. The method further includes calculating a difference between the first measurement of the inframarker and the baseline measurement of the inframarker. The method further includes, in response to the difference exceeding a predetermined delta, notifying that the subject has the physiological state.

According to one or more aspects, a computer-implemented method includes receiving, by one or more processors, from an optical monitoring device, an optical scan, wherein the optical scan comprises a first measurement of an inframarker, the inframarker is indicative of one or more optical measurements representative of a physiological identifier of a physiological state of a subject. The method further includes calculating, by the one or more processors, a difference between the first measurement of the inframarker and a baseline measurement of the inframarker, the baseline measurement being customized for the subject. The method further includes, in response to the difference exceeding a delta, notifying, by the one or more processors, that the subject has the physiological state.

According to one or more aspects, an analysis system includes a memory, and one or more processors coupled with the memory. The one or more processors access a plurality of optical scans of a subject, the subject known to have a physiological state, the optical scans captured by an optical monitoring device in a transdermal manner. Further, the one or more processors identify an infraprofile by analyzing the optical scans, the infraprofile is indicative of the physiological state of the subject the infraprofile comprises one or more inframarkers based on optical measurements from the optical scans. Further, the one or more processors output the infraprofile as a non-invasive identifier of the physiological state of the subject.

Other aspects and examples of the technical solutions described herein implement features of the above-described method in computer systems and computer program products.

The above features and advantages, and other features and advantages, of the present teachings are readily apparent from the following detailed description of some of the best modes and other embodiments for carrying out the present teachings, as defined in the appended claims, when taken in connection with the accompanying drawings.

BRIEF DESCRIPTION OF THE DRAWINGS

The subject matter is particularly pointed out and distinctly claimed at the conclusion of the specification. The foregoing and other features, and advantages of the present disclosure are apparent from the following detailed description taken in conjunction with the accompanying drawings in which:

The diagrams depicted herein are illustrative. There can be many variations to the diagrams or the operations described therein without departing from the spirit of the system and methods described herein. For instance, the actions can be performed in a differing order, or actions can be added, deleted, or modified. Also, the term "coupled" and variations thereof describes having a communications path between two elements and does not imply a direct connection between the elements with no intervening elements/connections between them. All of these variations are considered a part of the specification.

DETAILED DESCRIPTION

Aspects of technical solutions described herein facilitate using transdermal infrared optics to discover infraspectral markers. The infraspectral markers are associated with one or more diseases in some examples. An infraspectral marker can also be referred to herein as an inframarker. For example, the presence of one or more infraspectral markers in a transdermal scan of a subject, performed according to one or more aspects described herein, can be mapped to a disease or physiological state of the subject, such as, cancer, diabetes, a chronic condition, a comorbidity, a rare disease, or any other condition. An "inframarker" as used herein is an optical infrared signature representative of a biomarker e.g., troponin-I. An inframarker can be any form of infrared signature such as an absorption, a transmission, a reflection, or a combination thereof. For example, a unique combination of absorption peaks from an infraspectral scan can be inframarkers for biomarkers such as, h-FABP (fatty acid binding protein) or CEA (carcinoembryonic antigen). It is understood that other types of inframarkers and biomarkers can be used in other aspects of the technical solutions described herein. Further, "an infraprofile" refers to an optical infrared signature representative of a physiological condition e.g., Myocardial Infarction. An infraprofile can include one or more inframarkers. For example, a physiological condition can be represented by one or more biomarkers, and accordingly, the infraprofile for that physiological condition includes the corresponding one or more inframarkers. It will be appreciated that an inframarker may not necessarily have to represent a known biomarker. Some aspects of the technical solutions described herein can identify a unique inframarker profile that represents a physiological state of the subject 205 without corresponding to any known biomarker. In other words, the infraprofile facilitates identifying a physiological state of the subject 205 directly (without having to determine a corresponding biomarker).

Figure 2:
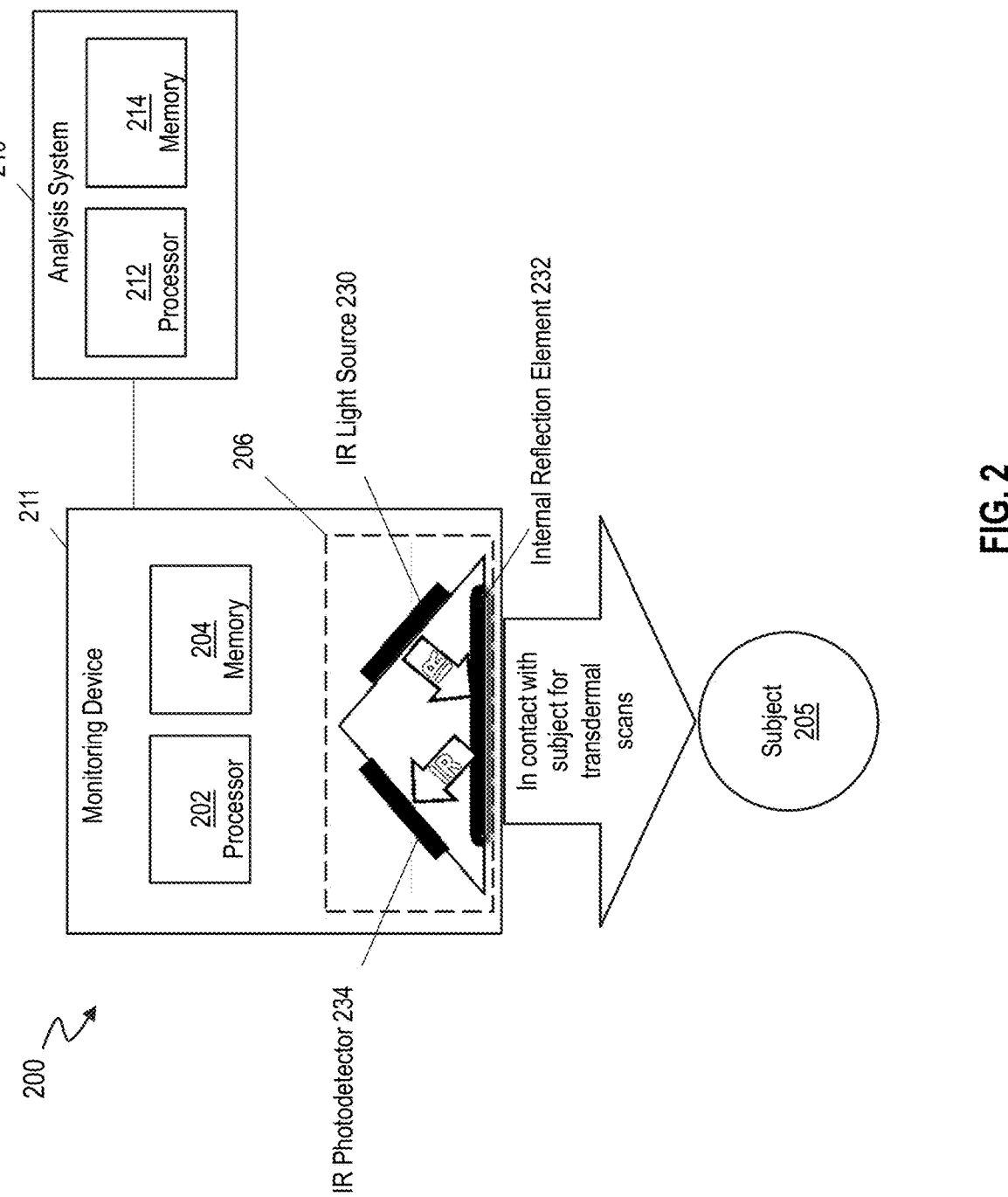
FIG. 2 depicts a block diagram for a system that includes a monitoring device for capturing a transdermal optical scan of a subject according to one or more aspects of the present technical solutions.
Figure 3:
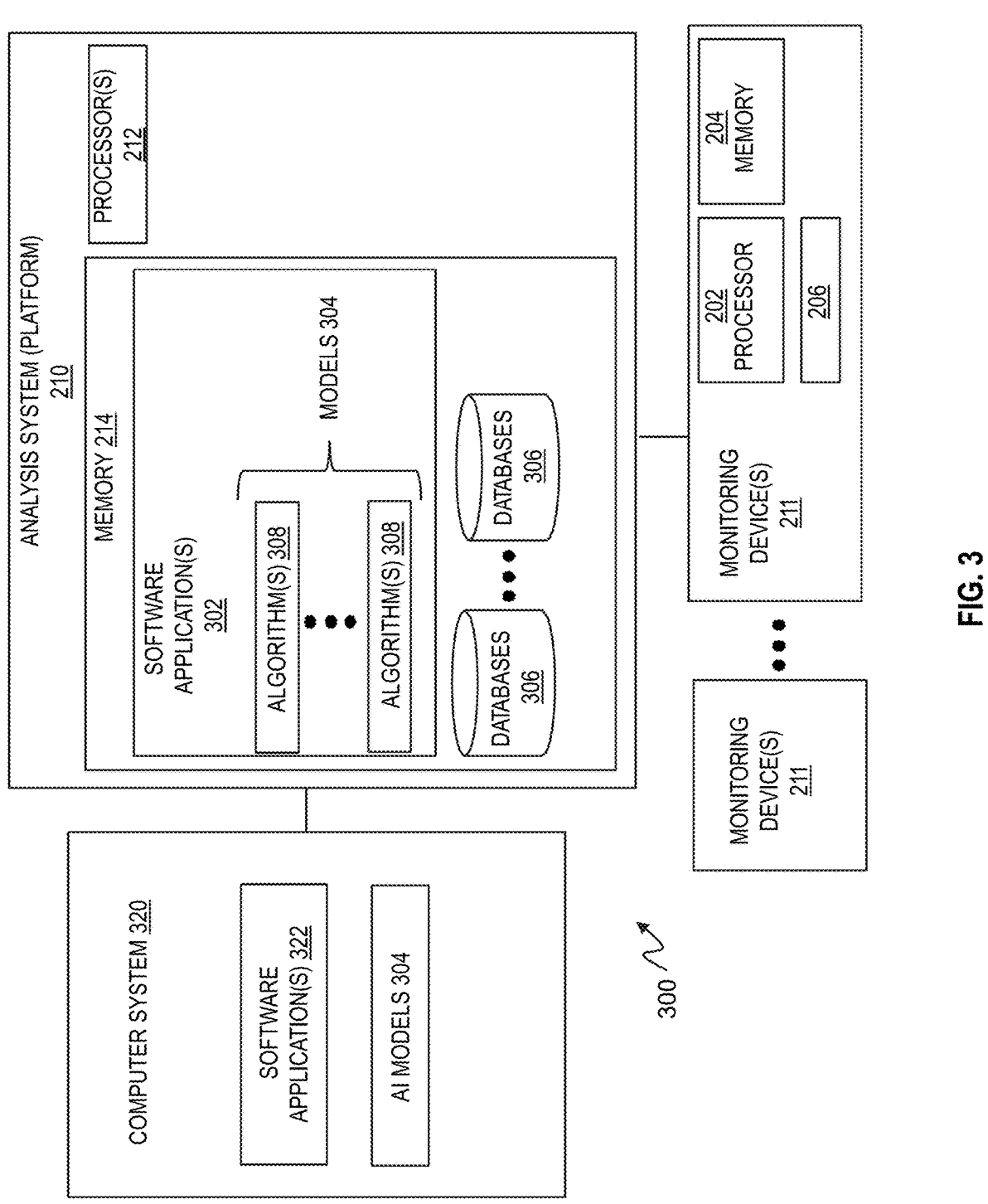
FIG. 3 depicts a block diagram for the system of FIG. 2 that includes software applications and algorithms executable as instructions providing a transdermal biomarker detection platform for use in conjunction with one or more aspects of the present technical solution.

Treatment of the disease or condition is applied to the subject (a person or patient) based on the detection of one or more infraspectral markers ("inframarkers"). According to one or more embodiments, a transdermal biomarker detection platform, generally indicated at 300 in FIG. 3, is provided that uses one or more infraspectral markers, an inframarker profile that is based on the infraspectral markers, and an inframarker configuration for one or more monitoring devices 211, the monitoring device 211 having an infraspectral sensor 206 used to perform the transdermal scan and detect the infraspectral marker of the subject, as shown in FIG. 2. An inframarker profile can also be referred to herein as an infraprofile. The inframarker configuration for the monitoring device 211 can be configured or set in various ways. In an illustrative example, the inframarker configuration can be a representation of a disease journey (series of disease phenotypes). In one example depicted in FIG. 5, the inframarker configuration can represent five inframarker profiles ("infraprofiles") for, respectively, five stages of cancer (precancerous, stages 1, 2, 3, 4). In another example depicted in FIG. 4, the inframarker configuration can represent three infraprofiles for, respectively, three stages of heart attack disease progression (baseline stable chronic ischemic heart disease, transient ischemic attack/ischemia, myocardial infarction).

Figure 4:
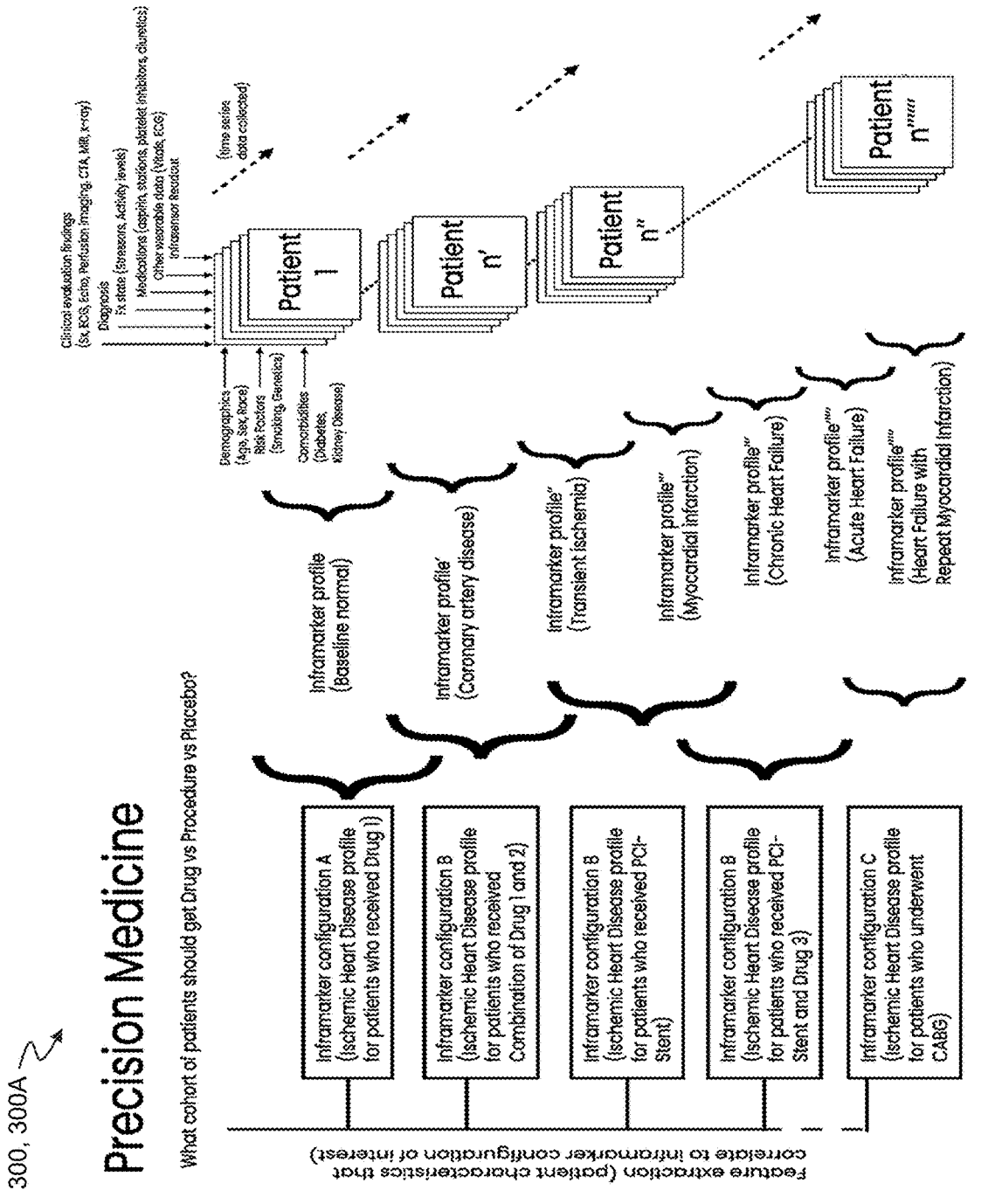
FIG. 4 depicts a block diagram of example interrelationships between disease and patient cohorts in a transdermal biomarker detection platform related to precision medicine as determined according to one or more aspects of the present technical solutions.

By using the infraspectral markers, inframarker profiles based on the infraspectral markers, and the inframarker configuration for the monitoring device, the transdermal biomarker detection platform 300 includes an analysis system 210 that is configured to provide precision medicine for a person (which could be a patient), as depicted in FIG. 4. Advantageously, in providing precision medicine for a person using the monitoring device 211, disease phenotyping allows risk stratification for health care providers, effective risk modeling for payer, better patient outcomes (i.e., successful treatment of diseases), and a lower cost burden to the health system.

Figure 5:
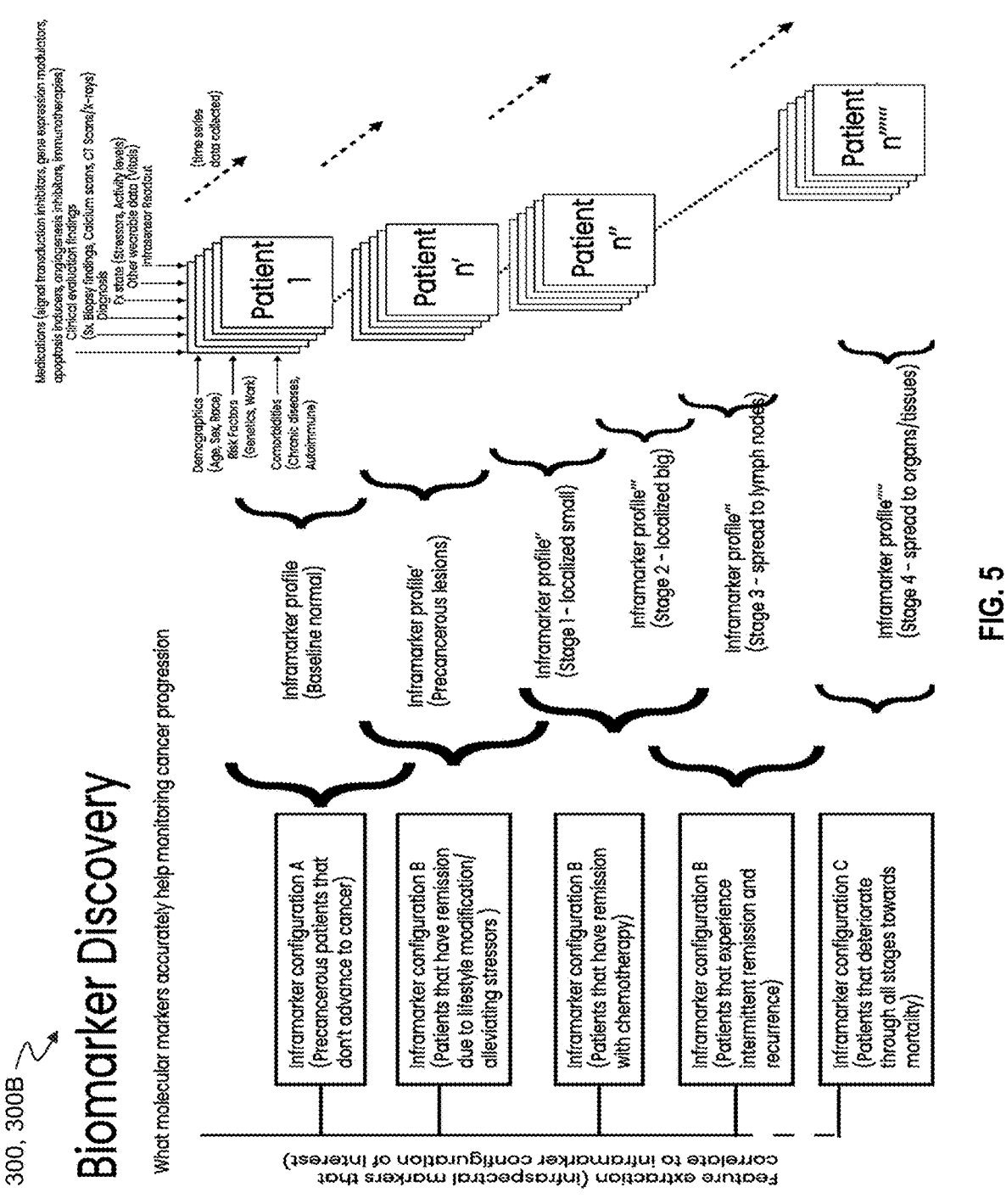
FIG. 5 depicts a block diagram of example interrelationships between disease and patient cohorts in a transdermal biomarker detection platform related to disease progression as determined according to one or more aspects of the present technical solutions.

By using the infraspectral markers, inframarker profile(s) based on the infraspectral markers, and the inframarker configuration for the monitoring device 211, the transdermal biomarker detection platform 300 includes an analysis system 210 that is configured to provide biomarker discovery, as depicted in FIG. 5. Particularly and advantageously, the analysis system 210 can identify molecular markers in chronic progressive diseases (such as cardiac and neurological diseases, diabetes, cancer, etc.), acute conditions of interest (such as infectious diseases, heart failures, sepsis, autoimmune diseases, etc.), etc. Targeted treatment can then be provided to the person according to the determined disease or condition.

Figure 6:
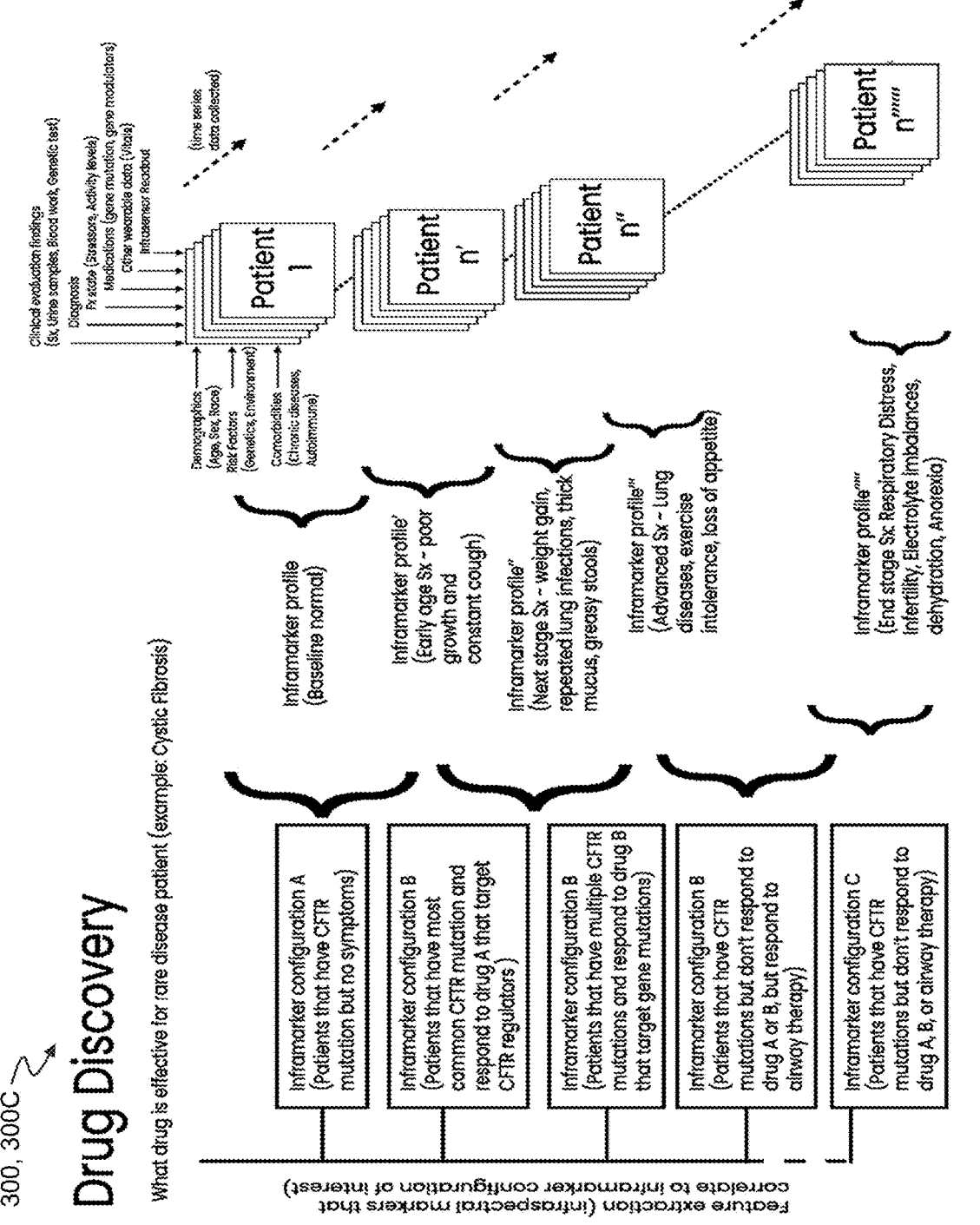
FIG. 6 depicts a block diagram of example interrelationships between disease and patient cohorts in a transdermal biomarker detection platform as related to drug effectiveness as determined according to one or more aspects of the present technical solutions.

By using the infraspectral markers, inframarker profile based on the infraspectral markers, and the inframarker configuration for the monitoring device 211, the transdermal biomarker detection platform 300 in one example, includes an analysis system 210 that is configured to facilitate drug discovery, as depicted in FIG. 6. Advantageously, drug discovery using the transdermal biomarker detection platform can be used in orphan drug development, optimal cancer treatment for circumventing cardio toxicity in tumor patients, and/or vaccine and drug development for infectious disease.

Additionally, by using the infraspectral markers, inframarker profile based on the infraspectral markers, and the inframarker configuration for the monitoring device, the transdermal biomarker detection platform 300 includes an analysis system 210 including a computer system 320 that is configured to provide advanced mathematical modeling to evaluate a drug or medical device (e.g., delivering a drug or controlling a bodily function such as the heart) where the evaluation can determine trending biomarkers, dosage levels, and the functional state of heart remodeling reversal.

Figure 1:
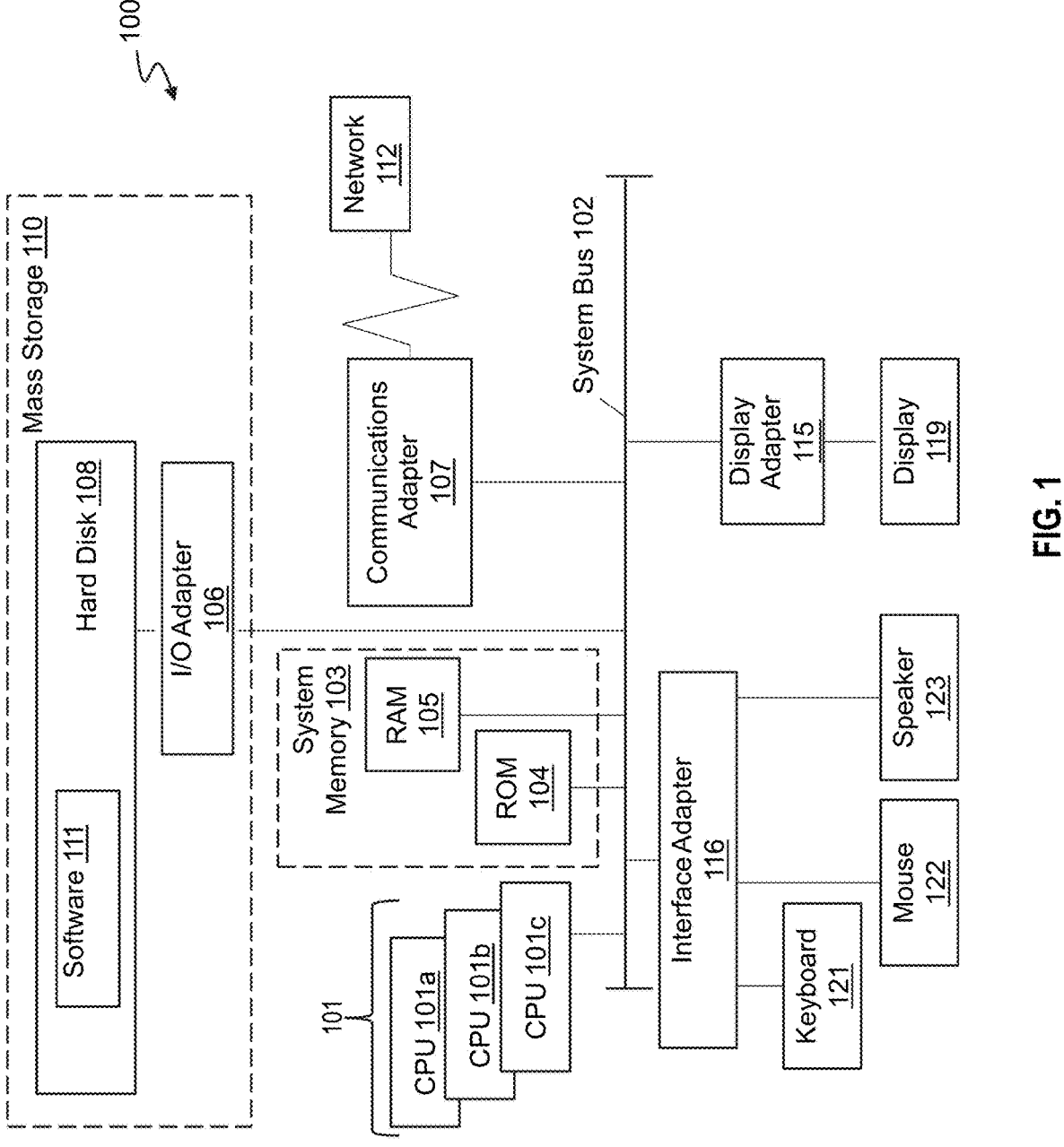
FIG. 1 depicts a block diagram of an example computer system for use in conjunction with one or more embodiments of the present technical solution.

FIG. 1 depicts a block diagram of an example computer system for use in conjunction with one or more example configurations of the system and/or methods described herein. In FIG. 1, a computer system 100 is generally shown in accordance with one or more configurations of the system and/or methods described herein. The computer system 100 can be an electronic, computer framework comprising and/or employing any number and combination of computing devices and networks utilizing various communication technologies, as described herein. The computer system 100 can be easily scalable, extensible, and modular, with the ability to change to different services or reconfigure some features independently of others. The computer system 100 may be, for example, a server, desktop computer, laptop computer, tablet computer, or smartphone. In some examples, computer system 100 may be a cloud computing node. Computer system 100 may be described in the general context of computer system executable instructions, such as program modules, being executed by a computer system. Generally, program modules may include routines, programs, objects, components, logic, data structures, and so on that perform particular tasks or implement particular abstract data types. Computer system 100 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, the computer system 100 has one or more central processing units (CPU(s)) 101a, 101b, 101c, etc., (collectively or generically referred to as processor(s) 101). The processors 101 can be a single-core processor, multi-core processor, computing cluster, or any number of other configurations. The processors 101, also referred to as processing circuits, are coupled via a system bus 102 to a system memory 103 and various other components. The system memory 103 can include a read only memory (ROM) 104 and a random access memory (RAM) 105. The ROM 104 is coupled to the system bus 102 and may include a basic input/output system (BIOS) or its successors like Unified Extensible Firmware Interface (UEFI), which controls certain basic functions of the computer system 100. The RAM is read-write memory coupled to the system bus 102 for use by the processors 101. The system memory 103 provides temporary memory space for operations of said instructions during operation. The system memory 103 can include random access memory (RAM), read only memory, flash memory, or any other suitable memory systems.

The computer system 100 comprises an input/output (I/O) adapter 106 and a communications adapter 107 coupled to the system bus 102. The I/O adapter 106 may be a small computer system interface (SCSI) adapter that communicates with a hard disk 108 and/or any other similar component. The I/O adapter 106 and the hard disk 108 are collectively referred to herein as a mass storage 110.

Software 111 for execution on the computer system 100 may be stored in the mass storage 110. The mass storage 110 is an example of a tangible storage medium readable by the processors 101. where the software 111 is stored as instructions for execution by the processors 101 to cause the computer system 100 to operate, such as is described herein below with respect to the various Figures. Examples of computer program product and the execution of such instruction is discussed herein in more detail. The communications adapter 107 interconnects the system bus 102 with a network 112, which may be an outside network, enabling the computer system 100 to communicate with other such systems. In one embodiment, a portion of the system memory 103 and the mass storage 110 collectively store an operating system, which may be any appropriate operating system to coordinate the functions of the various components shown in FIG. 1.

Additional input/output devices are shown as connected to the system bus 102 via a display adapter 115 and an interface adapter 116. In one embodiment, the adapters 106, 107, 115, and 116 may be connected to one or more I/O buses that are connected to the system bus 102 via an intermediate bus bridge (not shown). A display 119 (e.g., a screen or a display monitor) is connected to the system bus 102 by the display adapter 115, which may include a graphics controller to improve the performance of graphics intensive applications and a video controller. A keyboard 121, a mouse 122, a speaker 123, etc., can be interconnected to the system bus 102 via the interface adapter 116, which may include, for example, a Super I/O chip integrating multiple device adapters into a single integrated circuit. Suitable I/O buses for connecting peripheral devices such as hard disk controllers, network adapters, and graphics adapters typically include common protocols, such as the Peripheral Component Interconnect (PCI) and the Peripheral Component Interconnect Express (PCIe). Thus, as configured in FIG. 1, the computer system 100 includes processing capability in the form of the processors 101, and, storage capability including the system memory 103 and the mass storage 110, input means such as the keyboard 121 and the mouse 122, and output capability including the speaker 123 and the display 119.

In illustrative examples, the communications adapter 107 can transmit data using any suitable interface or protocol, such as the internet small computer system interface, among others. The network 112 may be a cellular network, a radio network, a wide area network (WAN), a local area network (LAN), or the Internet, among others. An external computing device may connect to the computer system 100 through the network 112. In some examples, an external computing device may be an external webserver or a cloud computing node.

It is to be understood that the block diagram of FIG. 1 is not intended to indicate that the computer system 100 is to include all of the components shown in FIG. 1. Rather, the computer system 100 can include any appropriate fewer or additional components not illustrated in FIG. 1 (e.g., additional memory components, embedded controllers, modules, additional network interfaces, etc.). Further, the embodiments described herein with respect to computer system 100 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments.

FIG. 2 depicts a block diagram for a system 200 that includes a monitoring device 211 for capturing a transdermal scan of a subject 205 according to one or more aspects of the present technical solutions. Any of the software and/or hardware features, including software 111, processors 101, memory/storage, etc., of computer system 100 may be incorporated in a monitoring device 211 and analysis system 210 of the system 200, as well as computer system 320 depicted in FIG. 3. The system 200 and platform 300 including the monitoring device 211, the analysis system 210, and the computer system 320 may include various software applications and/or algorithms, such as software 111 which can be executed as instructions on one or more processors 101 in order to perform according to one or more embodiments.

The system 200 includes, among other components that are not shown, a subject 205 (or user, also referred to herein as a person or patient), a monitoring device 211, and an analysis system 210. The subject 205 is a human user who is being analyzed to predict if the subject 205 has a particular physiological condition, or at least an infraspectral marker.

The monitoring device 211 can analyze the subject 205 by analyzing body fluids of the subject 205 in a transdermal manner. Bodily fluids of the subject 205 may include blood, intestinal fluid, etc. The monitoring device 211 includes a processing unit 202, a memory 204, and a sensor 206, among other components. It should be noted that although one each of the processing unit 202, the memory 204, and the sensor 206 are shown, in one or more examples, the monitoring device 211 can include multiple of one or more of those components. In addition, the monitoring device 211 can include other components such as connectors, communication devices, and the like, which are not shown.

The processing unit 202 can include one or more processors, such as a micro-processor, that can execute on or more computer executable instructions. The memory 204 is a volatile and/or non-volatile memory device that can store the computer executable instructions in addition to data items such as media, text, databases, data structures, files, and other electronic data that facilitates the operation of the monitoring device 211.

The sensor 206 is coupled with the processing unit 202 so that the processing unit 202 receives one or more sensor signals from the sensor 206. In one or more examples, the processing unit 202 sends instructions to the sensor 206, for example, to trigger the operation of the sensor 206. In one or more examples, the sensor 206 is an optical sensor that scans the body fluid of the subject 205 in a transdermal manner. The monitoring device 211 is in contact with the subject 205, for example, in contact with the skin of the subject 205, to facilitate the scanning by the sensor 206.

The monitoring device 211, using the sensor 206 transdermally detects one or more characteristics, such as proteins or other types of chemicals in the human body, for example, in the blood flow and interstitial fluids. The sensor 206 of the monitoring device 211 is not limited to an optical scanner. Other types of sensors 206 in the monitoring device 211 can include ECG sensors, haptic sensors, audio sensors, biosensors, and other types of sensors. In one or more aspects, the sensor 206 is a combination of sensors. The sensors can be placed at particular positions to measure the respective parameters of the subject 205. In some aspects, the sensors are placed in a specific configuration to facilitate receiving multiple measurement signals in parallel.

In one or more examples, the data from the sensors is transmitted in the form of electronic signals to an analysis system 210. The data may be stored in one or more databases 306 depicted in FIG. 3. The transmitted data includes the respective measurement signals from the one or more sensors, including the sensor 206. In one or more examples, the data is transmitted as streaming data. The electronic signals transmitted can be analog signals in one or more examples. Alternatively, or in addition, the electronic signals can include digital signals. Further, in one or more examples, the streaming data includes separate electronic signals from each of the multiple sensors that are embedded in the monitoring device 211. For example, the streaming data can include one or more ECG sensor signals and one or more biomarker sensor signals from the optical sensor 206. Other combinations of sensor signals are also possible in other aspects of the present technical solutions.

In one or more examples, the analysis system 210, based on the sensor signals, can determine an automated mapping between a phenotype for the patho-physiological condition (e.g., biomarker trends, phases of a disease, etc.) and infra-marker absorption intensities to identify an optimal infra-marker configuration for detecting this condition. An "infra-marker configuration" includes one or more settings of the monitoring device 211 to capture measurements (e.g., absorption, reflection, etc.) for an inframarker using total internal reflection. In some aspects, the measurements captured for an inframarker can be a set of one or more units of wavelength in the optical scan/measurements (i.e., infraspectral scan). The inframarker configuration can further include a value of a "delta" associated with an infra-marker, wherein the delta is a dynamic range used to determine if there is a spike/dip in the inframarker measurement, which corresponds to a spike/dip in the amount of the corresponding biomarker in the subject 205. In one or more aspects, the analysis system 210 performs the identification of the inframarker configuration, including determining the delta, using static algorithms or dynamic algorithms. Here, the inframarker absorption intensities are obtained based on the measurements from the optical sensor 206 of the monitoring device 211. In some aspects, an inframarker can be a predetermined set of one or more wavelengths in the optical measurements (i.e., infraspectral scan) of the monitoring device 211. The identification of the configuration is performed using machine learning (e.g., neural network) (e.g., using the machine learning of artificial intelligence models 304 depicted in FIG. 3) in one or more aspects, or adjusted by clinicians via a visualization tool by the analysis system 210.

In one or more aspects, an "inframarker configuration" can be discovered by the analysis system 210 for certain markers associated with a biological condition and stored in one of more databases 306 depicted in FIG. 3. For example, a unique combination of infraspectral scan generated peaks for biomarkers, such as, FABP (fatty acid binding protein) or CEA (carcinoembryonic antigen), can be identified. It is understood that other biomarkers are possible in other aspects.

In one or more aspects, the inframarker configuration can be identified for a certain inframarker associated with a physiological state when certain conditions are determined to be satisfied using machine learning techniques. For example, the inframarker configuration is generated when the transdermal infrared spectral scans includes a vector A (input measurements) that is mapped to known concentrations of a blood based protein as vector B (output). The inframarker configuration includes a vector in latent space that represents the ideal combination of optical measurements (e.g., infraspectral peaks, absorption values, etc.) that generates vector B from vector A. The inframarker configuration could also be generated via static or other dynamic techniques where various combinations of measurements from the transdermal optical scans are correlated with blood concentration levels using techniques such as regression analysis.

In other aspects, "inframarkers" indicative of a condition (phenotype) can be identified by the analysis system 210 and stored in one or more databases 306 depicted in FIG. 3. In one or more aspects, the delta value facilitates detecting a condition associated with one or more inframarkers indicative of a condition (phenotype). For example, the condition can be a relatively elevated level of an inframarker. For example, the condition can be an elevated Troponin level that is indicative of myocardial infarction, or elevated BNP that is indicative of acute heart failure. It is understood that the above conditions are exemplary, and that other conditions can also be used to identify corresponding inframarkers. A unique combination of infraspectral scan generated peaks (representing multiple biomarkers—these could be CRP, FABP, CTNI, CK-MB) can be identified for each particular condition or a combination of conditions. The identified inframarker(s) in this manner can be referred to as an "inframarker profile" for that condition or combination of conditions. The inframarker profile can also be referred to herein as an infraprofile. The infraprofiles can be identified using the system 200 for a particular condition or a combination of conditions. The inframarker profile ("infraprofile") can be stored in one or more databases 306.

Further, a time series analysis of an infraspectral scan can identify an underlying phase of a disease (another phenotype) using the analysis system 210. For example, a unique combination of optical measurements (e.g., relative peak, dip, etc.) in the transdermal infraspectral scan can identify coronary artery disease in its stable chronic state vs a reversible state of ischemia (acute myocardial injury) vs an irreversible state of ischemia (myocardial infarction) vs an ischemia in a state of reinfarction. In another example, the inframarker(s) facilitate identifying as the abnormal cells of a tumor spread to tissue and involve various levels of lymph nodes before metastasizing i.e., stage 1 cancer vs stage 2 cancer vs stage 3 cancer vs stage 4 cancer. Such identification, of different stages of a disease, can be achieved by using the aspects of the technical solutions described herein based on different infra markers released by the subject 205 in the different stages. For example, myocardial ischemia can release h-FABP, CRP, suPAR while infarction releases CTNI in addition to hFABP, CRP and suPAR. Stage 3 cancer (localized) releases certain signals and biomarkers while stage 4 (regional spread) and stage 5 (metastasized) release other signals and biomarkers. Based on the detection of these biomarkers (i.e., patho-physiological conditions) transdermally, using monitoring device 211, and in a continuous manner, technical solutions described herein facilitate improved triage and treatment of the conditions, along with remote patient monitoring for these conditions.

An inframarker configuration can include one or more settings (of the monitoring device 211) to be used to predict presence (or absence) of the physiological condition such as a biomarker in the subject 205 using a transdermal scan. Typically, in existing techniques, detecting a biomarker is performed using invasive tests such as, drawing blood or other types of fluids or matter from the subject. Further, detecting the biomarker is performed offline, in a clean laboratory environment, and can require a delay until the report comes back. This delay can be potentially delaying the subject 205 from receiving treatment, and in some cases, the "correct" treatment based on the information conveyed by the presence/absence of the biomarker.

Aspects of the present technical solutions address such challenges by facilitating a prediction of the presence/absence of the biomarker faster and in a non-invasive manner by performing a transdermal scan of the subject using the monitoring device 211. The monitoring device 211 is configured based on the physiological condition(s) to be detected. In some aspects, the monitoring device 211 is automatically reconfigured through a list of configurations respectively used to predict a list of physiological conditions. The list of physiological conditions can be input, and in one or more examples, the configurations of the monitoring device can be automatically changed, or adjusted by clinicians via a visualization tool. The configuration of the monitoring device 211 can be input directly on the monitoring device 211 using any input device including a touch screen graphical display, a keyboard, etc., and/or transmitted to the monitoring device 211 from the analysis system 210. When transmitted from the analysis system 210 (or any other device), the configuration for the monitoring device 211 can be input using an input device.

It should be noted that although the analysis system 210 is shown separate from the monitoring device 211, in one or more examples, the analysis system 210 can be part of the monitoring device 211 itself (or vice versa). In the cases where the analysis system 210 is separate from the monitoring device 211, the analysis system 210 can be a computing device, such as a server computer, a desktop computer, a laptop computer, a tablet computer, a phone, or any other such electronic device that includes a processing unit 212 and a memory 214. The processing unit 212 includes one or more processors that execute computer executable instructions. The memory 214 includes volatile/non-volatile memory device that facilitates the execution of the computer executable instructions. In one or more examples, the memory 214 stores the computer executable instructions. Further, the memory 214 can include media, text, databases, data structures, files, and other such electronic data to facilitate the execution of the computer executable instructions.

The one or more settings in the inframarker configuration to predict the physiological condition can include one or more wavelengths of light to be emitted by the monitoring device 211. The inframarker configuration can further include one or more thresholds respectively for the one or more wavelengths being used to scan the subject 205. A threshold is used to predict whether the subject 205 may have the physiological condition by comparing a corresponding measurement from the sensor 206 with that threshold. In some examples, the prediction may be based on a combination of measurements.

In one or more examples, the optical sensor 206 uses spectroscopy such as in near, mid, and far-infrared range, microwave range, visible region, or other such range of the electromagnetic spectrum. The range can be varied based on the biomarker (i.e., protein/chemical) being predicted. The optical sensor 206 uses infrared (IR) spectroscopy that provides an optical fingerprint of the biomarker when scanned in the 2000 to 800 cm–1 (5 μm to 12.5 μm) range. This detection can be used to identify, differentiate and quantify the amount of the biomarkers (for example, troponin I, FABP3, etc.) in whole blood. An inframarker is a fingerprint for a biomarker, and can be a unique combination of absorbance peaks within a spectral range in which the concentration of the biomarker in a biofluid can be detected using the optical sensor 206. Absorbance peaks are monitored based on amplitude of the reflected light that is absorbed by a photodetector in the optical sensor 206 in one or more examples.

In one or more examples, the optical sensor 206 includes at least the following components: an IR light source 230 and an IR photodetector 234. The IR source 230 can include lasers, light emitting diodes (LEDs), radiative light sources, or other such sources of IR light. For detecting particular biomarkers one or more absorbance peaks may be identified at predetermined wavelengths of the IR light. For example, two absorbance wavelength ranges, 5.5 to 6.6 μm and 8.3 to 11.8 μm are sensitive and specific to FABP3 in whole blood. Further, three absorbance wavelength ranges for troponin in whole blood are 5.5 μm to 7.8 μm, 8.8 μm to 10.3 μm, and 10.5 to 12 μm. The IR source 230 uses such predetermined wavelengths to facilitate detection of the corresponding biomarkers.

It is understood that the above described values are examples and that in one or more examples, different and/or additional wavelengths and/or ranges can be used. In one or more examples, the IR light source 230 transmits IR light of a particular wavelength based on a voltage that is applied to the IR light source 230. The voltage being applied to the IR light source 230 can be controlled by the processing unit 202, in one or more examples. The processing unit 202 applies a particular voltage depending on the biomarker that is being detected by the processing unit 202.

The IR photodetector 234 can include quantum wells, quantum dots, bolometers, and the like. The IR photodetector 234 is paired (maximum sensitivity) with the IR light source 230. In one or more examples, the IR photodetector 234 generates a voltage or an electric current as an output signal, which is proportional to an amount of light incident on the IR photodetector 234, after some of the light is absorbed by the subject 205. The IR photodetector 234 provides absorption measurements of the IR light from the body fluid(s) of the subject 205. The processing unit 202, and or the analysis system 210 predicts whether a biomarker is present in the subject 205 based on the absorption measurement. The processing unit 202 and/or the analysis system 210 further can stratify the subject 205 based on absorption measurement.

In some examples, the sensor 206 can also include an internal reflection element (IRE) 232 that is made of particular material(s) to facilitate the optical sensor 206 to detect the biomarker(s). For example, the IRE 232 can be made of low density polyethylene, diamond, ZnSe, Ge, Si etc. The IRE 232 is formed such that the IR light from the IR light source 230 is incident at an angle equal to or lesser than the critical angle associated with the IRE material to allow total internal reflection of the IR light. The critical angle is dependent on the material of the IRE 232. Further, the refractive indices of the IRE 232 and of the sample being analyzed, coupled with the wavelength of IR light dictate the penetration depth of the IR light into the tissue, blood (or any other body fluid) of the subject 205.

It is understood that other optical components and filters such as notch filters (selective wavelength) and polarizers are also used by the optical sensor 206 to improve the selectivity and sensitivity of the optical sensor 206 when detecting the biomarker. Such components are not shown in the drawings.

In one or more aspects of the present technical solutions, once one or more transdermal scans of the subject are performed, the analysis system 210 can generate an infraprofile of the subject 205. The infraprofile of the subject 205 saved to the database 306, and associated, for example, in the database 306 with other subject-related information of the subject 205. As shown in FIGS. 4-6, subject related information of a subject 205 (such as Patient 1) can include personally identifying information. demographics, risk factors, comorbidities, medications prescribed to or taken by the subject 205, clinical evaluation findings, and/or other data such as vitals obtained from a wearable device, all or some of which can be associated with the infraprofile of the subject 205 and the transdermal scans performed of the subject 205 and/or inframarkers detected for the subject 205. As determined by the analysis system 210, the infraprofile can predict the presence/absence of one or more biomarkers, and in turn, physiological conditions of the subject 205. Based on the infraprofile, a medical personnel (e.g., doctor, nurse, etc.) or the analysis system 210 can recommend a treatment, test, etc., for the subject. For example, based on the prediction from the transdermal scan, the medical personnel or the analysis system 210 may determine whether an invasive test is required. Alternatively, or in addition, based on the prediction, the medical personnel or the analysis system 210 can determine a certain course of treatment for the subject 205. See illustrative examples shown in FIGS. 4-6.

In some cases, the transdermal scan can be performed in a continuous manner by the monitoring device 211, for example, a transdermal scan is performed at predetermined intervals. Based on the measurements from the continuous monitoring, trends of the biomarkers can be non-invasively determined by the analysis system 210 at predetermined intervals. Accordingly, real time analysis and prediction of the biomarker (i.e., physiological condition) of the subject 205 can be performed in a continuous manner, using the monitoring device 211 and the analysis system 210. Here "continuous manner" includes performing at least two transdermal optical scans every minute in some aspects. In other words, within a certain predetermined duration, at least two transdermal optical scans are performed, where the predetermined duration can be one of 45 seconds, 60 seconds, 90 seconds, 120 seconds, 150 seconds, 180 seconds, 300 seconds, or any other such predetermined duration. In yet other words, two successive transdermal optical scans are performed within a predetermined interval of each other such as 45 seconds, 60 seconds, 90 seconds, 120 seconds, 150 seconds, 180 seconds, 300 seconds, or any other such predetermined interval. It is understood that other intervals can be selected.

Aspects of the present technical solutions further facilitate personalized triage and alert workflow baseline and trending information. For example, a baseline of the measurements from the monitoring device 211 for a particular subject 205 can be established by capturing the transdermal optical scans of the subject 205 for at least a predetermined times/ duration. For example, once at least 15 transdermal optical scans are performed for the subject 205, those 15 scans are used to establish baseline measurements for a particular biomarker (e.g., troponin I, FABP3, etc.) for the subject 205. Subsequently, further transdermal optical scans (e.g., the 16th scan) of the subject 205 are compared to the established baseline to determine whether a change (delta) in one or more measurements exceeds (spike/dip) a predetermined threshold. In such cases, further actions can be taken for the subject 205. In other examples, instead of a personalized baseline, a predetermined baseline can be used to compare the trends of the measurements of the subject 205. A separate baseline (personalized or predetermined) is used for each measurement captured in the non-invasive transdermal optical scan. In some cases, a personalized baseline (for a particular subject) is used for a first inframarker (e.g., h-FABP) and a predetermined baseline (non-personalized/common across multiple subjects) is used for a second inframarker (e.g., troponin I).

Figure 7:
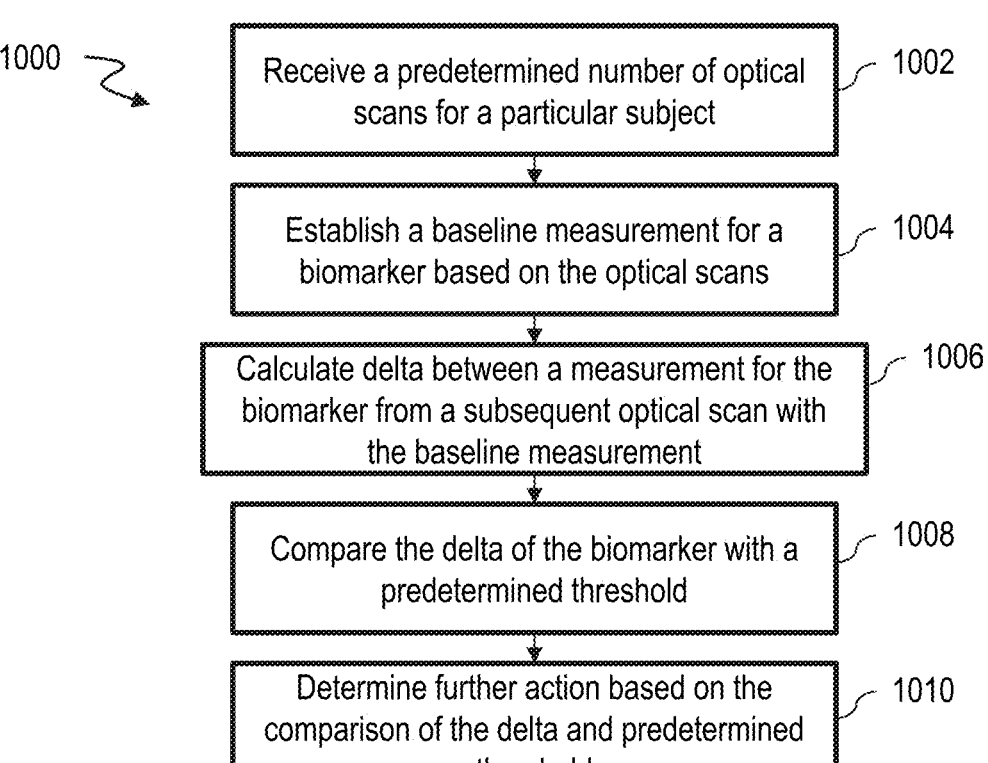
FIG. 7 depicts a flowchart of a method for continuous monitoring a subject for one or more biomarkers using the optical sensing system according to one or more aspects.

FIG. 7 depicts a flowchart of a method for continuous monitoring a subject for one or more biomarkers using the optical sensing system according to one or more aspects. See also FIGS. 4-6 depicting aspects of the technical solutions and method described herein. The method 1000 includes, at block 1002, receiving, by the analysis system 210, data from at least a predetermined number of optical scans performed on a particular subject 205. The predetermined number can be 5, 10, 15, or any other number that the analysis system 210 can use to establish a personalized baseline measurement for the subject 205. The data from the optical scans, which can also be referred to herein as infrasensor data, can be saved to the database 306, and as previously described, can be associated in the database 306 with subject-related information of the particular subject 205.

At block 1004, the analysis system 210 establishes the baseline measurement for at least one inframarker, i.e., biomarker (e.g., troponin I) using the optical scans, e.g., the infrasensor data collected during optical scans of the subject 205 using the monitoring device 211. The baseline measurement is established using a statistical technique such as calculating the mean, geometric mean, weighted mean, trendline computation, logistic regression, or any other linear or non-linear statistical computation. In some aspects, the baseline is established using machine learning, for example, using algorithms such as multi-parameter deep neural network.

In some aspects, when using machine learning to establish the baseline, the analysis system 210 automatically adjusts the monitoring device 211. The configurability of the monitoring device 211 can facilitate adjusting one or more settings such as delta value, wavelength of the light emitted and/or detected, intensity of light, electric voltage, electric current, pulse rate of the light emitter, pulse rate of the light receiver, etc. Here, the delta value is used to compare deviations of the measurements from the personalized baseline(s), and in response to the deviation being larger than the delta value, triggering one or more actions as described herein.

The analysis system 210 can conduct a predetermined number of optical scans of the subject 205 using a particular inframarker configuration, i.e., settings of the monitoring device 211. The captured optical scans are analyzed to establish the baseline measurements. If a satisfactory baseline measurement (e.g., comparing with ground truth data) cannot be established for a physiological identifier of the subject 205 using the machine learning algorithm, the inframarker configuration of the monitoring device 211 is adjusted by the analysis system 210, and the baseline establishment is repeated using the machine learning. Such a process is repeated until a satisfactory baseline is established for a physiological marker of the subject 205. In some examples, a baseline measurement is established for multiple physiological markers for the subject in this manner.

At block 1006, data from subsequent optical scans by the monitoring device 211 is compared by the analysis system 210 with the established baseline to calculate a difference between a measurement corresponding to the physiological identifier (e.g., biomarker) being observed with the baseline measurement. It should be noted that in some aspects, the difference can be based on measurements of multiple parameters. For example, the physiological identifier can be based on measurements of two or more units of wavelengths. Accordingly, the delta can be based on (e.g., mean, sum, median, etc.) of the differences between measurements of the two or more parameters in a transdermal optical scan and corresponding baseline measurements.

At block 1008, the calculated difference is compared with a predetermined threshold, i.e., the delta value. If the difference exceeds the delta, a spike or a dip can be identified. In some aspects, an absolute value (modulus) of the difference is used to compare with the delta.

At block 1010, a further action is determined based on the comparison of the difference and the delta. For example, if a spike/dip is not identified, i.e., the difference does not exceed the delta value, the continuous monitoring is continued. Alternatively, if a spike/dip is detected, additional tests may be performed on the subject 205. In yet other aspects, in case of the spike/dip being detected, the configuration of the monitoring device 211 is adjusted to perform additional optical scans on the subject 205. In some examples, if the difference exceeds the delta only by a minimal amount (e.g., a second predetermined value), the configuration of the monitoring device 211 is adjusted automatically to detect fluctuations and/or variations from the baseline. In some aspects, if the delta is exceeded, a notification to the medical personnel and/or to the subject 205 can be triggered. The notification can be transmitted, for example, via a display or interface accessible by the medical personnel and/or the subject 205, or via an alert output by the monitoring device 211.

The analysis system 210 can access the configurability of the monitoring device 211 and adjust one or more settings of the monitoring device 211 and request additional optical scans using the adjusted settings. For example, the adjustments can include changing the wavelengths of light emitted and/or detected, intensity of light, internal angles of reflection, electric voltage applied, electric current, or any other setting that can cause a particular measurement to be captured in a more accurate manner. Such automatic configurability (i.e., adjustment of configuration) of the monitoring device can improve accuracy of the detecting a physiological identifier/marker for the subject 205 in the optical scan (i.e., non-invasive, transdermal manner). In some cases, a user, such as a nurse, clinician, doctor, or any other personnel, can review and/or update the adjustments being made to the monitoring device 211. For example, the user can view the adjustments to the settings of the monitoring device 211 via a user-interface, for example, a display of the analysis system 210. The user can make additional changes to the adjusted settings, which are subsequently sent by the analysis system 210 to the monitoring device 211.

Alternatively, or in addition, frequency of capturing the transdermal optical scans can also be changed in response to the delta being within a predetermined range. For example, frequency of capturing and analyzing the transdermal optical scans is lower (e.g., scan every 15 minutes) when the delta is in a first predetermined ("safe") range, whereas when the delta is in a second predetermined ("critical") range, the frequency of capturing and analyzing the transdermal optical scans is adjusted higher (e.g., scan every five minutes). It is understood that additional predetermined ranges and corresponding monitoring frequencies can be used in other aspects of the technical solutions herein. In some aspects, in addition to updating the frequency, alert notifications/reports for subject 205 are sent to medical personnel and/or caregivers.

In some aspects, the analysis system 210 already knows that the subject 205 has a certain physiological state, e.g., a disease. The analysis system 210, in conjunction with the monitoring device 211, can be used to determine an inframarker configuration (i.e., settings of the monitoring device 211) that can detect an inframarker in the optical scans for the subject, i.e., a measurement in the subject 205 that corresponds to the physiological state.

Figure 8:
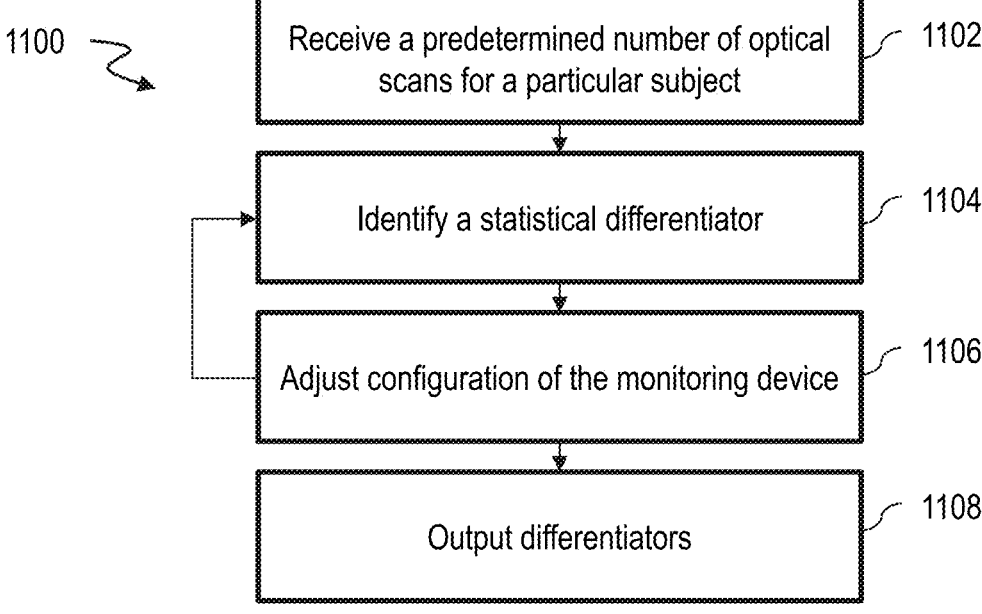
FIG. 8 depicts a flowchart of a method for establishing an inframarker configuration for a physiological state according to one or more aspects.

FIG. 8 depicts a flowchart of a method 1100 for establishing an inframarker configuration for a physiological state according to one or more aspects. The analysis system 210 causes the monitoring device 211 to capture at least a predetermined number of optical scans of the subject 205 using a first configuration (i.e., settings) of the monitoring device 211, at block 1102. At block 1104, the measurements from the optical scans are analyzed to identify one or more differentiators, e.g., spikes, dips, trends, or any other statistically relevant markers. The differentiators are identified using machine learning, in one or more examples. In some examples, temporal analysis of time series data using recurrent neural network (RNN) is performed to identify the one or more differentiators. In some examples, the RNN identifies various differentiators that can serve as predetermined thresholds (delta values) for appropriate trigger actions (higher frequency monitoring and analysis/alerts/notifications/reporting.

At block 1106, the analysis system 210 adjusts one or more settings of the monitoring device 211 to generate a second inframarker configuration. In one or more aspects, the second inframarker configuration is generated in response to differentiators not being identified using the first inframarker configuration. In some aspects, the analysis system 210 continues to generate additional inframarker configurations until one or more differentiators are identified. Alternatively, or in addition, the analysis system 210 generates at least a predetermined number of inframarker configurations. One or more differentiators are sought (see block 1104) after each change in configuration.

At block 1108, after a predetermined number of configurations, after a predetermined duration, or in response to a manual intervention, the analysis system 210 exits the loop (1104, 1106), and outputs the identified differentiators.

In some aspects, the configuration of the monitoring device 211 for identifying a physiological state is used automatically when a subject 205 with that physiological state is being monitored by the monitoring device 211.

Aspects of the present technical solutions further facilitate remote patient monitoring. For example, the monitoring device 211 can be used by the subject 205 when s/he is away from a medical institution (e.g., hospital, research institute, etc.). The measurements from the monitoring device 211 can be transmitted to the analysis system 210, which may or may not be remote from the monitoring device 211. The infra-profile that is generated may be transmitted to a medical personnel, who may be remote from the subject (and hence, monitoring device 211) and suggest the further course of action for the subject 205. Also, the analysis system 210 may analyze the measurements and apply and/or cause further treatment to be applied.

One or more aspects of the technical solutions described herein facilitate the use of transdermal biomarker detection for the treatment of disease and/or disease progression, according to one or more embodiments. FIG. 3 depicts a block diagram of the system 200 illustrating further details of the analysis system 210 according to one or more embodiments. Some details of the monitoring device 211 are omitted in FIG. 3 for the sake of clarity but operate as discussed herein.

The analysis system 210 may operate as a transdermal biomarker detection platform 300 that uses deep infraomics. The analysis system 210 can include one or more software applications 302 configured to perform deep infraomics, along with any of the analysis discussed herein. Deep infraomics, as that term is used herein, is artificial intelligence based a digital platform that builds on top of infraomics. Infraomics, as that term is used herein, is the study of infraspectral markers ("inframarkers", e.g., molecular markers characterized by infrared wavelengths), inframarker profiles ("infraprofiles", e.g., for a specific disease phenotype), and inframarker configurations (e.g., the characterization of disease progression including phases of cardiovascular disease, neurological disease, cancer, etc.).

Now turning to an example as depicted in FIG. 4, in which the monitoring device 211 is configured to scan for biomarkers (i.e., infraspectral markers) associated with the heart, the heart can go through characteristic patho-physiological phases (phenotypes): baseline normal->coronary artery disease->transient ischemia->myocardial infarction->heart failure. In each of these phenotypes different biomarkers may be expected. So, baseline normal might have baseline troponins; coronary artery disease might have mildly elevated baselines for troponins; transient ischemia might have a subtle rise and fall of troponins while having an appreciable rise in ischemia markers such as FABP, and inflammatory markers like suPar, CRP; myocardial infarction might have an acute rise of troponins, FABP, CRP, suPar. However, the levels of these over time will vary by virtue of their half-life and renal clearance. Heart failure might then have mildly elevated baseline for troponin and another biomarker BNP that is released when the myocardium experiences stretch due to heart's response to increased afterload or preload. Since the levels of these different markers vary in different phases of the diseases, and is further variable based on patient's clinical context that varies with time, the software application 320 (e.g., AI models 304) are configured for deep learning in which the AI models 304 include neural networks (e.g., convolutional neural networks (CNNs)) coupled with time series analysis (long short-term memory (LSTM), recurrent neural network (RNN), etc.) to understand the complex relationships (e.g., a researcher may be unable to see continuous biomarkers that are representative of true underlying patho-physiology). Once the biomarkers for the different phases are determined using the monitoring devices 211 and analysis system 210, the analysis system 210 can cause treatment/medicine to be administered for any subject determined to be experiencing any of the determined patho-physiological phases of the heart.

Using infraspectral markers, one or more inframarker profiles ("infraprofiles") and/or one or more inframarker configurations, the software applications 302 may include and/or be coupled to one or more algorithms configured to perform and provide precision medicine, biomarker discovery, drug discovery, and/or in silico clinical trials as technical solutions.

Further regarding use of the analysis system 210 and one or more monitoring devices 211 for providing precision medicine, the software application 302 is configured to use infrasensor generated data (captured by the monitoring device 211) in the form of infraprofiles stored in the database 306 to enable disease phenotyping with the relevant clinical context using deep infraomics in a transdermal biomarker detection platform 300. One or more computer systems 320 of healthcare providers can leverage this platform provided by the analysis system 210 to risk stratify patients and provide care for better patient outcomes. The computer system 320 of payers and capitated healthcare systems can develop risk models to identify clinical management workflows that provide best patient outcomes with optimal economic value.

As an example scenario regarding precision medicine, FIG. 4 depicts a block diagram of example interrelationships that exist between disease and patient cohorts as determined using one or more monitoring devices 211 and the analysis system 210 according to one or more embodiments. Use of the monitoring device 211 and analysis system 210 provides an illustrative transdermal biomarker detection platform 300A that allows extracting relevant features to guide, for example, precision medicine for the subject 205. Although the precision medicine example is for heart disease, it should be appreciated that precision medicine can be applied to any disease, thereby customizing healthcare, with medical decisions, treatments, procedures, or pharmacotherapeutics being tailored to a subgroup of patients. Software application 302 is configured to perform feature extraction by capturing (after scanning by the monitoring device 211) the desired infraspectral markers that correlate to the inframarker configuration of interest. In FIG. 4, the one or more monitoring devices 211 have been set for the inframarker configuration that scans the subject 205 for the inframarkers associated with the heart disease profile, such as inframarker configuration A, B, C. The software applications 302 of the analysis system 210 are configured to receive the inframarkers from the monitoring device(s) 211 and determine inframarker profiles for each stage. The software application 302 may compare the received inframarker profile of the subject 205 to a previously known inframarker profile for the heart stored in one or more databases 306, in order to determine which patho-physiological phase the subject 205 is experiencing. According to the specific patho-physiological phase for the heart, the analysis system can cause treatment/medicine to be administered for the subject 205 (i.e., patient). In determining the specific patho-physiological phase for the heart of the subject, software applications 302 are configured to account for various factors associated with other previous patients 1–n (patient cohorts) that may affect the determination for the current subject 205.

Further regarding use of the analysis system 210 and one or more monitoring devices 211 for facilitating biomarker discovery, the software application 302 is configured to utilize deep infraomics to allow researchers (using one or more computer systems 320) in identifying infraspectral markers (e.g., molecular markers with characteristic fingerprint regions in the infrared spectrum) of interest. These could be biomarkers specific to an infectious disease or cancer, for example. One or more software applications 322 of computer system 320 for clinicians can use deep infraomics (provided by the analysis system 210) to develop infraprofiles for disease states to identify acute conditions in emergency settings such as emergency departments, operating rooms, and intensive care units. Computer systems 320 of clinicians using deep infraomics (provided by the analysis system 210) can also develop inframarker configurations to understand transition through chronic disease states and identify optimal medical management for patient cohorts as they go through phases of disease progression such as in diabetes, benign to metastatic cancer progression, neurological degeneration, or cardiovascular heart remodeling. Deep Infraomics coupled with infrasensors (e.g., monitoring devices 211) can now allow real time monitoring of disease progression for the subject 205 (i.e., the patient).

As an example scenario regarding biomarker discovery, FIG. 5 depicts a block diagram of example interrelationships that exist between disease and patient cohorts as determined using one or more monitoring devices 211 and the analysis system 210 according to one or more embodiments. Use of the monitoring device 211 and analysis system 210 provides an illustrative transdermal biomarker detection platform 300B that allows extracting relevant features to guide, for example, biomarker discovery for what biomarkers (e.g., molecular markers) that accurately help monitor cancer progression. Although the biomarker discovery example is for cancer, it should be appreciated that the biomarker discovery can be for any disease, at any stage, with or without comorbidities. Again, software application 302 is configured to perform feature extraction by capturing (after scanning by the monitoring device 211) the desired infraspectral markers that correlate to the inframarker configuration of interest. In FIG. 5, the one or more monitoring devices 211 have been set for the inframarker configuration that scans the patients for the inframarkers associated with the cancer profile, such as inframarker configuration A, B, C. The software applications 302 of the analysis system 210 are configured to receive the inframarkers from the monitoring device(s) 211 and determine inframarker profiles for each stage. The software application 302 may compare the received inframarker profiles of respective patients to their known health condition, in order to determine which patho-physiological phase (i.e., stage of cancer) that the respective patients are experiencing. According to the specific patho-physiological phase of cancer, the analysis system 210 can accurately discover which specific biomarkers are associated with each stage of cancer.

Further regarding use of the analysis system 210 and one or more monitoring devices 211 for facilitating drug discovery to treat diseases, the software application 302 provides a deep infraomics platform that is engineered to accelerate clinical trials and enable new treatments for patients needing therapeutic management such as patients suffering from rare diseases with no known care workflow identified. For example, the software application 302 of the deep infraomics platform accelerates clinical trials and enable better treatments for cancer patients that suffer cardiotoxicity. The software applications 302 of the deep infraomics platform accelerates clinical trials and treatments in drugs and vaccines for new infectious disease/viral outbreaks. In one example, the monitoring device 211 can be configured to discover a multiple biomarker panel and potentially other biomarkers that need to be discovered longitudinally in rare diseases. The software applications 302 executing the AI mode(s) 304 determines that the biomarker panel (i.e., multiple biomarkers) correlate to a rare disease such as, for example Gaucher disease or Fabry disease.

As an example scenario regarding drug discovery, FIG. 6 depicts a block diagram of an example of what drug is effective for a rare disease patient (e.g., cystic fibrosis) as determined using one or more monitoring devices 211 and the analysis system 210 according to one or more embodiments. Use of the monitoring device 211 and analysis system 210 provides a provides an illustrative transdermal biomarker detection platform 300C that allows extracting relevant features to guide, for example, the discovery of what drug is effective for the treatment of the disease. Although the drug discovery example is for cystic fibrosis, it should be appreciated that the drug discovery applied to any disease. As noted herein, the software application 302 is configured to perform feature extraction by capturing (after scanning by the monitoring device 211) the desired infraspectral markers that correlate to the inframarker configuration of interest. In FIG. 6, the one or more monitoring devices 211 have been set for the inframarker configurations that scans the patients for the inframarkers associated with the cystic fibrosis disease profile, such as inframarker configurations A, B, C. The software applications 302 of the analysis system 210 are configured to receive the inframarkers from the monitoring device(s) 211 and determine inframarker profiles for each stage of the disease. The software application 302 may compare the received inframarker profiles of the patients in the cohorts to the known health conditions for the respective patients, in order to determine the effectiveness of respective drug A, drug B, and/or drug A and drug B. According to the response of the treatment, the analysis system 210 can determine which drugs and/or drug combination is beneficial for the treatment of cystic fibrosis. In determining the effective treatment for cystic fibrosis, software applications 302 are configured to account for various factors associated with patients 1–n (patient cohorts) that may affect the effectiveness of the respective drugs.

Further regarding use of the analysis system 210 and one or more monitoring devices 211 for facilitating in silico trials, the software application 302 using deep infraomics provides advanced mathematical modeling on a proprietary dataset (e.g., stored in databases 306) that includes time series infraspectral markers, infraprofiles, and inframarker configurations through the patient life cycle of disease, along with the clinical context around disease management, clinical findings, drug dosage, demographics, and risk factors. The software application 302 (and/or the software application 322) can perform retrospective and prospective analysis, which allow drug companies and research institutions to run in-silico trials to accelerate the evaluation of new drugs and/or medical devices and/or interventions prior to in-human trials. Using the software applications 302, deep infraomics generates prognosis scores and extrapolates clinical end points for drug and device manufacturers, regulatory bodies, and payers to assess investment into new drugs and pharmaceuticals. By visualizing patient impact, deep infraomics will enable researchers and healthcare providers in determining appropriate dosage of a pharmacologic therapeutic or the optimal time to intervene with a procedure (treatment plan), thereby personalizing care workflows based on patient baselines. The treatment plan can be further modulated on a frequent basis, based on the patient's dynamic infraprofile.

There can be many approaches to build deep infraomics using the analysis system 210 with the monitoring device 211, and any of the approaches can be utilized collectively, individually, and/or in any desired combination.

In one or more examples, the analysis system 210 of the system 200 may utilize decentralized data collection from infrasensors (e.g., monitoring devices 211) with inputs for clinical context. Infrasensor generated data (e.g., infraspectral markers) with patient related features is used to build a large dataset (e.g., stored in one or more databases 306) for different clinical queries (infraprofiles and inframarker configurations). Using the large dataset (e.g., stored in one or more databases 306) for different clinical queries (infraprofiles and inframarker configurations), the software applications 302 are configured to enable users to query different clinical questions to understand the effect of drugs or any other clinical variables.

In one or more examples, the analysis system 210 of the system 200 may utilize centralized data normalization and foundational machine learning architecture. Various machine learning models including artificial intelligence (AI) models 304 are developed and used with the deep infraomics platform. For example, one or more software applications 302 can have one or more algorithms 308 trained and configured to operate as the AI model 304. Software application 302 (including the AI model 304) is configured to allow users to query and simulate different scenarios. Particularly, software application 302 is configured to perform feature extraction by capturing (after scanning by the monitoring device 211) the desired infraspectral markers that correlate to the inframarker configuration of interest. Infrasensor (e.g., monitoring devices 211) along with other wearables (e.g., ECG, vital signs) generate time series data. Foundational deep learning models (e.g., AI models 304) based on this time series information when coupled with patient features provide a unique view into the patient's patho-physiology of disease progression over time. The software applications 302 (e.g., AI models 304) can be leveraged by different stakeholders (e.g., one or more computer systems 320 having software applications 322 configured to communicate and interact with software applications 302) such as pharma companies to query the data to ask different questions, to simulate different scenarios, and/or to perform in silico clinical trials.

In one or more embodiments, the analysis system 210 of the system 200 may be configured to provide deployable AI models. For example, the AI models 304 can be deployed from the analysis system 210 to one of more computer systems 320 in order for the deployed AI models 304 to run completely and/or partially on the computer systems 320. Open access APIs can allow licensing and commercial access to digital platform and commercial collaboration. Computer systems 320 of pharmaceutical companies can use machine learning models developed on top of the deep infraomics platform of the analysis system 210. Computer systems 320 can also customize/finetune the models with their own dataset. The analysis system 210 can also be deployable to help pharmaceutical companies perform different in silico experiments.

In one or more embodiments, one or more algorithms 308 of software application(s) 302 individually and/or working in any combination may be implemented as so-called classifiers (described in more detail below). In one or more embodiments, the features of the one or more AI/machine learning models 304 described herein can be executed by processors discussed herein, or can be implemented on a neural network (not shown). In illustrative examples of the system, methods and technical solutions described herein, the features software application 302 (e.g., AI/machine learning models 204) can be implemented by configuring and arranging the processor to execute machine learning (ML) algorithms (e.g., algorithms 308). In general, ML algorithms, in effect, extract features from received data (e.g., inputs to the software application 302) in order to "classify" the received data. Examples of suitable classifiers include but are not limited to neural networks (described in greater detail below), support vector machines (SVMs), logistic regression, decision trees, hidden Markov Models (HMMs), etc. The end result of the classifier's operations, i.e., the "classification," is to predict a class for the data. The ML algorithms apply machine learning techniques to the received data in order to, over time, create/train/update a unique "model." The learning or training performed by the software applications 302 (algorithms 308 of models 304) can be supervised, unsupervised, or a hybrid that includes aspects of supervised and unsupervised learning. Supervised learning is when training data is already available and classified/labeled. Unsupervised learning is when training data is not classified/labeled so must be developed through iterations of the classifier. Unsupervised learning can utilize additional learning/training methods including, for example, clustering, anomaly detection, neural networks, deep learning, and the like.

In one or more embodiments algorithms 308 are implemented as neural networks, a resistive switching device (RSD) can be used as a connection (synapse) between a pre-neuron and a post-neuron, thus representing the connection weight in the form of device resistance. Neuromorphic systems are interconnected processor elements that act as simulated "neurons" and exchange "messages" between each other in the form of electronic signals. Similar to the so-called "plasticity" of synaptic neurotransmitter connections that carry messages between biological neurons, the connections in neuromorphic systems, such as neural networks, carry electronic messages between simulated neurons, which are provided with numeric weights that correspond to the strength or weakness of a given connection. The weights can be adjusted and tuned based on experience, making neuromorphic systems adaptive to inputs and capable of learning. For example, a neuromorphic/neural network for handwriting recognition is defined by a set of input neurons, which can be activated by the pixels of an input image. After being weighted and transformed by a function determined by the network's designer, the activations of these input neurons are then passed to other downstream neurons, which are often referred to as "hidden" neurons. This process is repeated until an output neuron is activated. Thus, the activated output neuron determines (or "learns") which character was read. Multiple pre-neurons and post-neurons can be connected through an array of RSD, which naturally expresses a fully-connected neural network.

Various aspects of the technical solutions are described herein with reference to the related drawings. Alternative aspects of the technical solutions can be devised without departing from the scope of this technical solutions. Various connections and positional relationships (e.g., over, below, adjacent, etc.) are set forth between elements in the following description and in the drawings. These connections and/or positional relationships, unless specified otherwise, can be direct or indirect, and the present technical solutions are not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

One or more of the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

For the sake of brevity, conventional techniques related to making and using aspects of the technical solutions may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2 % of a given value.

The present technical solutions may be a system, a method, and/or a computer program product at any possible technical detail level of integration. The computer program product may include a computer readable storage medium (or media) having computer readable program instructions thereon for causing a processor to carry out aspects of the present technical solutions.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present technical solutions may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present technical solutions.

Aspects of the present technical solutions are described herein with reference to flowchart illustrations and/or block diagrams of methods, apparatus (systems), and computer program products according to aspects of the technical solutions. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present technical solutions. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following provide example configurations of a method and system for using transdermal infrared optics to determine infraspectral markers, to configure a monitoring device according to an inframarker configuration for detecting a condition such as a disease state, to determine at least one infraspectral marker of a subject indicative of a physiological state of the subject; and to identify an infraprofile indicative of a physiological state of the subject based on infraspectral markers of the subject, as disclosed herein.

According to one or more aspects, a system includes a transdermal optical monitoring device, and an analysis system in communication with the transdermal optical monitoring device. The analysis system performs a method that includes receiving, from the transdermal optical monitoring device, a predetermined number of optical scans, each optical scan comprising data indicative of absorption of light by a subject, the absorption caused in response to the transdermal optical monitoring device transmitting light pulses towards the subject in a transdermal manner. The method further includes establishing a baseline measurement for an inframarker based on the data from the predetermined number of optical scans, the inframarker is indicative of a biomarker of a physiological state of the subject, the inframarker is based on one or more measurements from an optical scan. The method further includes receiving, from the optical monitoring device, a first optical scan comprising a first measurement of the inframarker. The method further includes calculating a difference between the first measurement of the inframarker and the baseline measurement of the inframarker. The method further includes, in response to the difference exceeding a predetermined delta, notifying that the subject has the physiological state.

In one or more aspects, the analysis system automatically adjusts one or more settings of the transdermal optical monitoring device.

In one or more aspects, the analysis system adjusts the one or more settings of the transdermal optical monitoring device to establish the baseline measurement of the inframarker.

In one or more aspects, the analysis system adjusts the one or more settings of the transdermal optical monitoring device in response to the difference being less than a second predetermined threshold.

In one or more aspects, the analysis system causes the optical monitoring device to capture at least two optical scans within a predetermined duration.

In one or more aspects, the predetermined duration is less than one minute.

In one or more aspects, the transdermal optical monitoring device is configured to generate light at a predetermined pulse rate and the transdermal optical monitoring device is configured to detect at a predetermined polling rate.

According to one or more aspects, a computer-implemented method includes receiving, by one or more processors, from an optical monitoring device, an optical scan, wherein the optical scan comprises a first measurement of an inframarker, the inframarker is indicative of one or more optical measurements representative of a physiological identifier of a physiological state of a subject. The method further includes calculating, by the one or more processors, a difference between the first measurement of the inframarker and a baseline measurement of the inframarker, the baseline measurement being customized for the subject. The method further includes, in response to the difference exceeding a delta, notifying, by the one or more processors, that the subject has the physiological state.

In one or more aspects, the physiological identifier comprises a biomarker for the physiological state.

In one or more aspects, the method further includes receiving, by the one or more processors, from the optical monitoring device, a predetermined number of optical scans. The method further includes customizing the baseline measurement of the inframarker for the subject based on the data from the predetermined number of optical scans.

In one or more aspects, the analysis system adjusts the one or more settings of the optical monitoring device to establish the baseline measurement of the inframarker.

In one or more aspects, the analysis system adjusts the one or more settings of the optical monitoring device in response to the difference being in a predetermined range.

In one or more aspects, the analysis system continuously monitors the subject by causing the optical monitoring device to capture at least two optical scans within a predetermined duration.

In one or more aspects, the optical monitoring device is configured to detect light at a range of 6.4-6.9 micrometers and a range of 8-14 micrometers in an optical scan.

According to one or more aspects, an analysis system includes a memory, and one or more processors coupled with the memory. The one or more processors access a plurality of optical scans of a subject, the subject known to have a physiological state, the optical scans captured by an optical monitoring device in a transdermal manner. Further, the one or more processors identify an infraprofile by analyzing the optical scans, the infraprofile is indicative of the physiological state of the subject. The infraprofile comprises one or more inframarkers based on optical measurements from the optical scans. Further, the one or more processors output the infraprofile as a non-invasive identifier of the physiological state of the subject.

In one or more aspects, the one or more processors are further configured to access a first optical scan of the subject, the first optical scan comprising a first measurement of an inframarker. The one or more processors further calculate a difference between the first measurement of the inframarker and a baseline measurement of the inframarker. The one or more processors, in response to the difference exceeding a delta, add the inframarker to the infraprofile of the physiological state.

In one or more aspects, the baseline measurement is customized for the subject.

In one or more aspects, the baseline measurement of the inframarker is customized for the subject based on the data from the predetermined number of optical scans.

In one or more aspects, the one or more processors are further configured to cause the optical monitoring device to collect optical scans continuously over a predetermined amount of time.

In one or more aspects, the one or more inframarkers includes is an inframarker configured as an optical infrared signature representative of a biomarker.

In one or more aspects, the optical infrared signature includes a combination of absorption peaks from an optical scan, and the combination is unique to the biomarker.

In one or more aspects, the one or more processors are further configured to store the infraprofile to a database, receive subject information related to the subject, and associate the subject information with the infraprofile in the database.

In one or more aspects, the subject information includes at least one of identifying information, demographics, comorbidities, clinical findings, diagnosis, medications, or vital data of the subject.

In one or more aspects, the analysis system further includes an inframarker configuration for configuring the monitoring device to detect an inframarker of the one or more inframarkers.

In one or more aspects, the one or more inframarkers include a first inframarker and an at least second inframarker; and the system further comprises a first inframarker configuration for configuring the monitoring device to detect the first inframarker of the subject, and an at least second inframarker configuration for configuring the monitoring device to detect the at least second inframarker of the subject.

In one or more aspects, the first inframarker predicts a first physiological state, and the at least second inframarker predicts an at least second physiological state which is different from the first physiological state.

In one or more aspects, the first inframarker is representative of a progression stage of a disease, and the at least second inframarker is representative of another progression stage of the disease.

In one or more aspects, the disease is cancer.

In one or more aspects, the disease is heart disease.

In one or more aspects, the first inframarker is associated with a first subject condition, and the at least second inframarker is associated with an at least second subject condition which is different from the first subject condition.

In one or more aspects, the first subject condition is a treatment of a disease administered to the subject, and the at least second subject condition is another treatment of the disease administered to the subject.

In one or more aspects, the treatment includes administering a drug to the subject, and the another treatment includes administering another drug to the subject, the another drug being different from the drug.

The descriptions of the various embodiments of the present technical solutions have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. An analysis system comprising:
a memory; and
one or more processors coupled with the memory, the one or more processors being configured to:
access a plurality of optical scans of a subject, the subject having a physiological state, the optical scans being captured by an optical monitoring device in a transdermal manner;

identify an infraprofile by analyzing the optical scans, wherein the infraprofile comprises an optical infrared signature representative of the physiological state of the subject, the infraprofile including one or more inframarkers derived from optical measurements from the optical scans, wherein the infraprofile identifies the physiological state directly based on the optical infrared signature independently of determining a corresponding biomarker or a composite of corresponding biomarkers; and
output the infraprofile as a non-invasive identifier of the physiological state of the subject;
access a first optical scan of the subject, the first optical scan comprising a first measurement of an inframarker;
calculate a difference between the first measurement of the inframarker and a baseline measurement of the inframarker, the baseline measurement of the inframarker being customized for the subject based on data from a predetermined number of optical scans; and
in response to the difference exceeding a delta, add the inframarker to the infraprofile of the physiological state; and
wherein the one or more inframarkers includes a specific inframarker configured as the optical infrared signature representative of a specific biomarker, and the optical infrared signature includes a combination of absorption peaks unique to the specific biomarker.

2. The analysis system of claim 1, wherein the one or more processors are further configured to:
store the infraprofile to a database;
receive subject information related to the subject; and
associate the subject information with the infraprofile in the database.

3. The analysis system of claim 2, wherein the subject information includes at least one of identifying information, demographics, comorbidities, clinical findings, diagnosis, medications, or vital data of the subject.

4. The analysis system of claim 1, further comprising:
an inframarker configuration for configuring the optical monitoring device to detect a selected inframarker of the one or more inframarkers.

5. The analysis system of claim 1, the one or more inframarkers including a first inframarker and an at least second inframarker; the analysis system further comprising:
a first inframarker configuration for configuring the optical monitoring device to detect the first inframarker of the subject;
an at least second inframarker configuration for configuring the optical monitoring device to detect the at least second inframarker of the subject.

6. The analysis system of claim 5, wherein:
the first inframarker predicts a first physiological state of the subject; and
the at least second inframarker predicts an at least second physiological state of the subject which is different from the first physiological state.

7. The analysis system of claim 6, wherein the first inframarker is representative of a progression stage of a disease; and
the at least second inframarker is representative of another progression stage of the disease.

8. The analysis system of claim 7, wherein the disease is cancer.

9. The analysis system of claim 7, wherein the disease is heart disease.

10. The analysis system of claim 5, wherein:

the first inframarker is associated with a first subject condition; and the at least second inframarker is associated with an at least second subject condition which is different from the first subject condition.

11. The analysis system of claim 10, wherein the first subject condition is a treatment of a disease, the treatment administered to the subject; and the at least second subject condition is another treatment of the disease, the another treatment administered to the subject.

12. The analysis system of claim 11, wherein the treatment includes administering a drug to the subject; and the another treatment includes administering another drug to the subject, the another drug being different from the drug.

13. The analysis system of claim 1, wherein the infraprofile represents the physiological state of the subject without corresponding to a known biomarker.

14. The analysis system of claim 1, wherein the one or more processors are further configured to identify the infraprofile using an inframarker configuration that repre-sents a disease journey comprising a series of disease phenotypes associated with the physiological state of the subject.

15. The analysis system of claim 14, wherein the one or more processors are further configured to support precision medicine by performing disease phenotyping and risk stratification for the subject based on the identified infraprofile and the inframarker configuration.

16. The analysis system of claim 14, wherein the one or more processors are further configured to facilitate drug discovery by analyzing infraprofiles derived from infraspectral markers across a plurality of subjects using the inframarker configuration.

17. The analysis system of claim 1, wherein the optical monitoring device captures the plurality of optical scans in the transdermal manner using infrared spectroscopy in a mid-infrared range of the electromagnetic spectrum to generate the optical measurements forming the inframarkers.

18. The analysis system of claim 17, wherein the mid-infrared range includes wavelengths from 5 micrometers to 12.5 micrometers.

* * * * *